United States Patent
Rieck

(10) Patent No.: US 10,532,153 B2
(45) Date of Patent: Jan. 14, 2020

(54) INSERTION DEVICE FOR INSERTION SET

(71) Applicant: MEDTRONIC MINIMED, INC., Northridge, CA (US)

(72) Inventor: Douglas A. Rieck, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 435 days.

(21) Appl. No.: 15/609,485

(22) Filed: May 31, 2017

(65) Prior Publication Data

US 2017/0258989 A1 Sep. 14, 2017

Related U.S. Application Data

(63) Continuation of application No. 14/134,879, filed on Dec. 19, 2013, now Pat. No. 9,694,132.

(51) Int. Cl.
*A61M 5/158* (2006.01)

(52) U.S. Cl.
CPC ..... *A61M 5/158* (2013.01); *A61M 2005/1583* (2013.01); *A61M 2005/1585* (2013.01)

(58) Field of Classification Search
CPC .......... A61M 5/158; A61M 2005/1585; A61M 2005/14252; A61M 5/2033
USPC ................... 604/135, 131, 134, 157
See application file for complete search history.

(56) References Cited

U.S. PATENT DOCUMENTS

| | | |
|---|---|---|
| 4,755,173 A | 7/1988 | Konopka et al. |
| 5,299,571 A | 4/1994 | Mastrototaro |
| 5,390,671 A | 2/1995 | Lord et al. |
| 5,391,250 A | 2/1995 | Cheney, II et al. |
| 5,482,473 A | 1/1996 | Lord et al. |
| 5,485,408 A | 1/1996 | Blomquist |
| 5,522,803 A | 6/1996 | Teissen-Simony |
| 5,586,553 A | 12/1996 | Halili et al. |
| 5,665,065 A | 9/1997 | Colman et al. |
| 5,800,420 A | 9/1998 | Gross et al. |
| 5,807,375 A | 9/1998 | Gross et al. |
| 5,851,197 A * | 12/1998 | Marano ................. A61M 5/158 604/135 |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |

(Continued)

*Primary Examiner* — Phillip A Gray

(74) *Attorney, Agent, or Firm* — Lorenz & Kopf, LLP

(57) ABSTRACT

An insertion device for use with an insertion set is provided. The insertion device includes a first housing having a rail. The insertion device includes a hub having a first end coupled to the rail and a second end including a projection. The hub is movable relative to the first housing along the rail. The insertion device includes a locking carrier in the first housing and movable between a first position and a second position. The locking carrier is coupled to the projection in the first position and the projection is released in the second position. The insertion device includes a second housing coupled to the insertion set and surrounding at least a portion of the first housing to define a gap. The locking carrier is received in the gap in the second position to release the projection of the hub and to enable the insertion set to be uncoupled.

20 Claims, 4 Drawing Sheets

(56) References Cited

U.S. PATENT DOCUMENTS

| | | |
|---|---|---|
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |
| 2013/0060105 A1 | 3/2013 | Shah et al. |

* cited by examiner

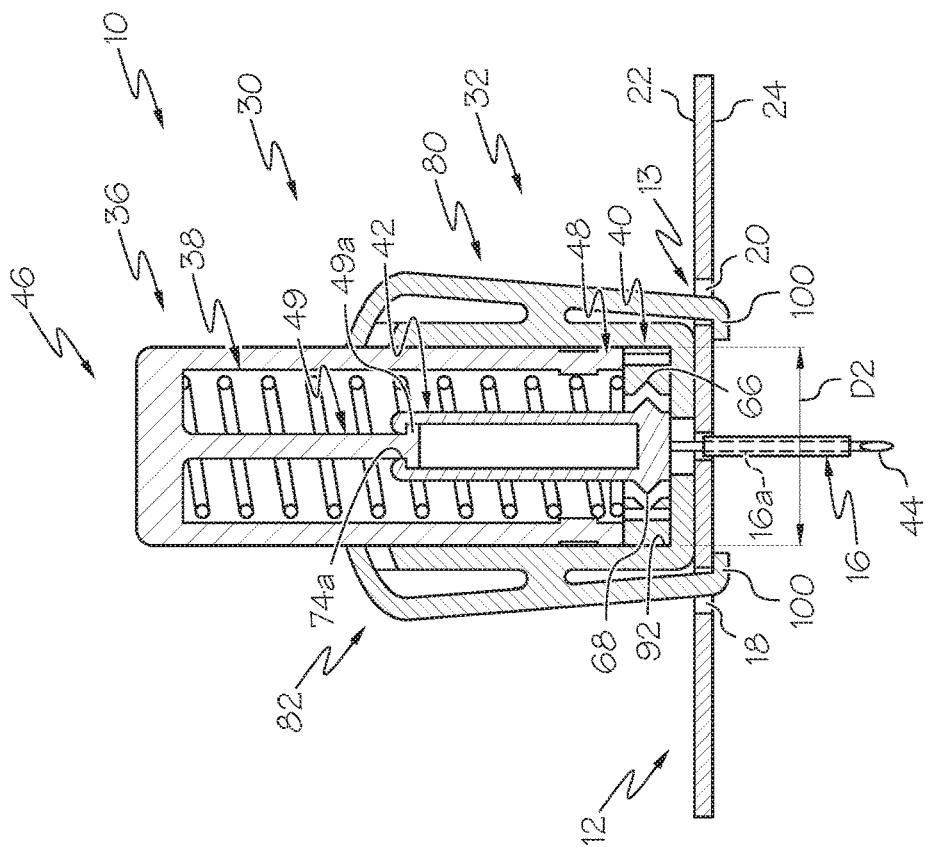
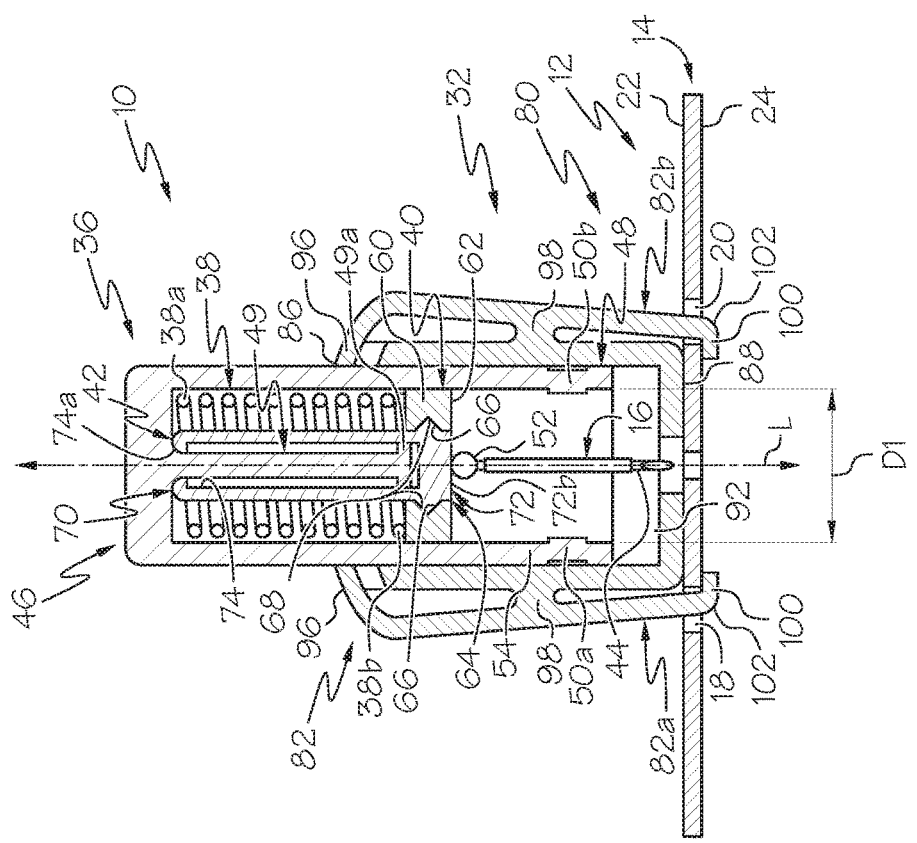

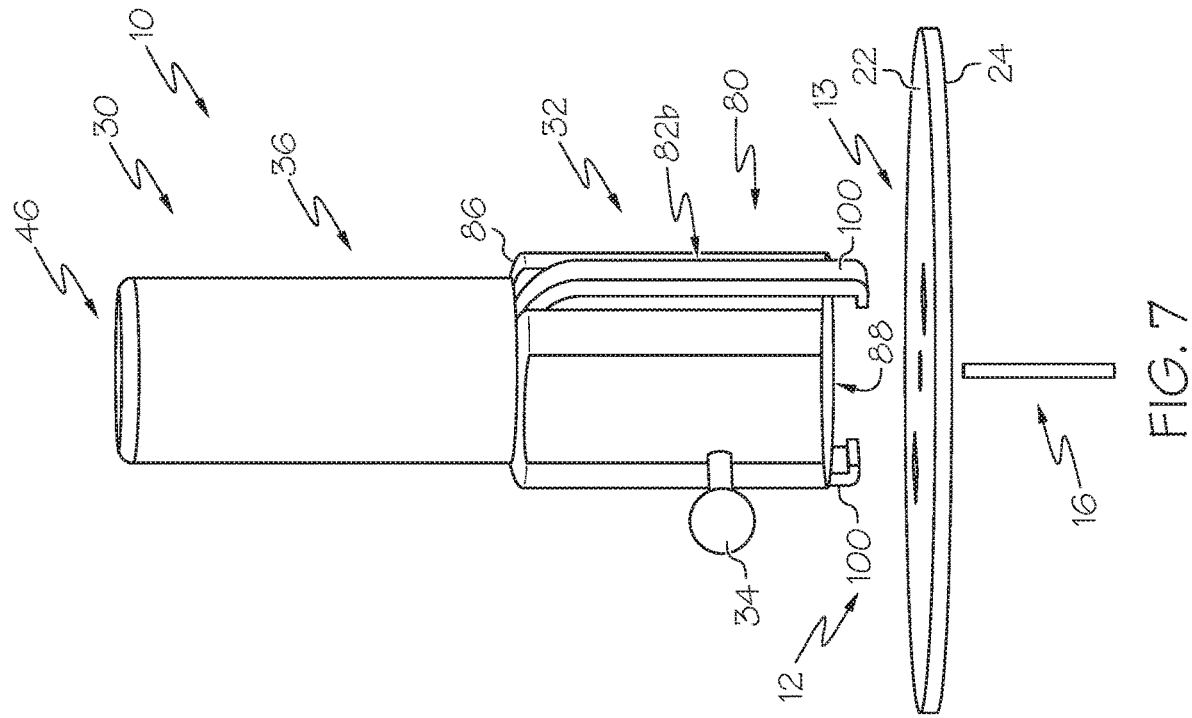
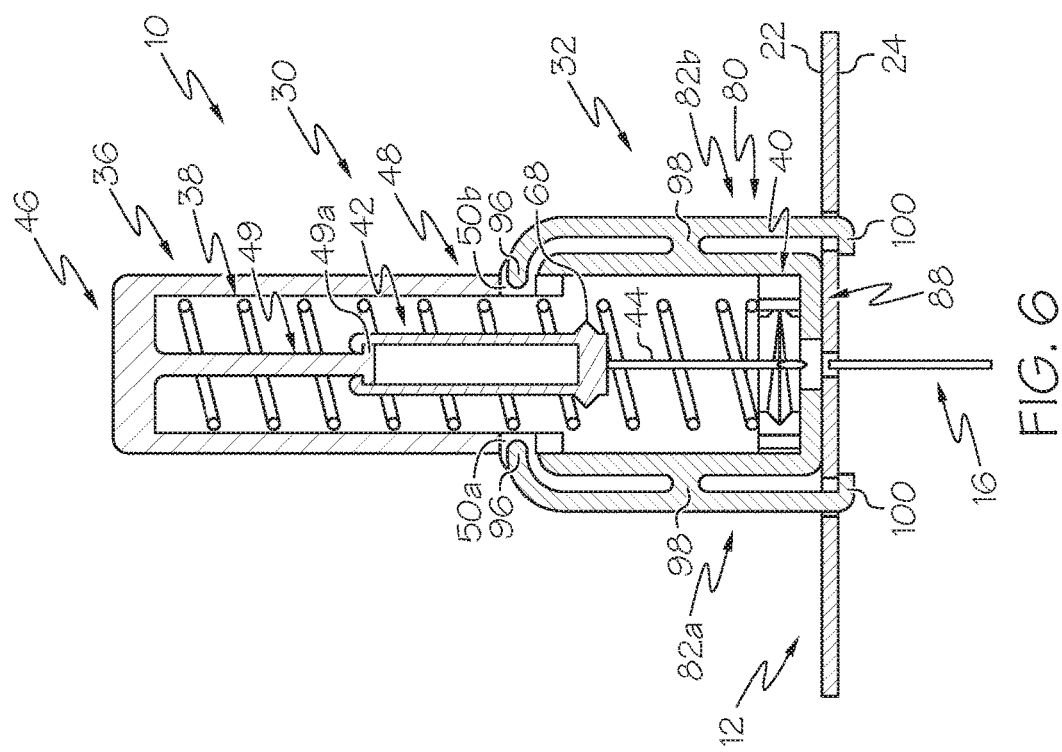

INSERTION DEVICE FOR INSERTION SET

CROSS-REFERENCE TO RELATED APPLICATIONS

This application is a continuation of U.S. patent application Ser. No. 14/134,879, filed on Dec. 19, 2013. The relevant content of the above application is incorporated by reference herein.

TECHNICAL FIELD

Embodiments of the subject matter described herein relate generally to insertion devices. More particularly, embodiments of the subject matter relate to an insertion device for an insertion set.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user. In certain instances, these fluid infusion devices require an insertion set, such as an infusion set, to be coupled to the body of a user for the delivery of the insulin. Typically, the infusion set requires a portion of a cannula, for example, to be inserted under the skin of the user to deliver the controlled amounts of insulin to the user.

In addition, in order to determine the proper amount of insulin to dispense via the manually operated syringes, insulin pens or insulin pumps, the glucose level of the user is monitored. Glucose levels may be monitored using manual devices, such as with test strips in combination with a blood glucose monitor, and/or may be monitored using an insertion set, such as a sensor set, that is coupled to a body of the user. Generally, in order to monitor glucose levels with a sensor set, at least a portion of the sensor set needs to be inserted under the skin of the user to measure glucose levels in interstitial fluid.

Accordingly, it is desirable to provide an insertion device for an insertion set for coupling the insertion set, such as an infusion set and/or a sensor set, to the body of the user. Furthermore, other desirable features and characteristics will become apparent from the subsequent detailed description and the appended claims, taken in conjunction with the accompanying drawings and the foregoing technical field and background.

BRIEF SUMMARY

According to various embodiments, an insertion device for use with an insertion set is provided. The insertion device includes a first housing and a first member received in the first housing and movable relative to the first housing between a first position and a second position. The insertion device also includes a second housing substantially surrounding at least a portion of the first housing such that a gap exists between the first housing and the second housing. The first member is received in the gap in the second position. The second housing has at least one locking arm to couple the insertion set to the second housing. The first member is movable from the first position to the second position to uncouple the insertion set from the housing.

Also provided according to various embodiments is an insertion device for use with an insertion set. The insertion device includes a first housing assembly movable between a first position, a second position and a third position. The first housing assembly including a first member coupled to a second member and a first housing. The first member is movable with the second member relative to the first housing from the first position to the second position. The insertion device also includes a second housing coupled to the first housing. The second housing includes at least one locking arm that couples the insertion set to the second housing when the first housing assembly is in the first position and the second position. The movement of the first housing assembly from the second position to the third position pivots the at least one locking arm into engagement with the first housing to uncouple the insertion set from the second housing.

Further provided according to various embodiments is an insertion device for use with an insertion set. The insertion device includes a first housing and a locking carrier disposed within the first housing and movable relative to the first housing. The insertion device includes a hub releasably coupled to the locking carrier and to the first housing to insert a portion of the insertion set. The insertion device also includes a biasing member coupled between an inner surface of the first housing and the locking carrier, and a second housing coupled to the first housing such that a gap exists between the first housing and the second housing. The second housing includes at least one locking arm that couples the insertion set to the second housing. The biasing member biases the locking carrier and the hub from a first position within the first housing to a second position. In the second position, the locking carrier is uncoupled from the hub.

In various embodiments, an insertion device for use with an insertion set is provided. The insertion device includes a first housing having a rail that extends within the first housing along a longitudinal axis of the insertion device. The insertion device includes a hub having a first end coupled to the rail and a second end to be coupled to an insertion instrument. The hub is movable relative to the first housing along the rail and the second end includes a projection. The insertion device includes a locking carrier received in the first housing and movable relative to the first housing between a first position and a second position. The locking carrier is coupled to the projection in the first position and the projection is released from the locking carrier in the second position. The insertion device includes a second housing coupled to the insertion set and surrounding at least a portion of the first housing to define a gap between the first housing and the second housing. The locking carrier is received in the gap in the second position to release the projection of the hub from the locking carrier and to enable the insertion set to be uncoupled from the second housing.

Also provided is an insertion device for use with an insertion set. The insertion device includes a first housing having a rail that extends within the first housing along a longitudinal axis of the insertion device. The insertion device includes a hub having a first end coupled to the rail and a second end to be coupled to an insertion instrument. The hub is movable relative to the first housing along the rail and the second end includes a projection. The insertion device includes a locking carrier received in the first housing and movable relative to the first housing between a first position and a second position. The locking carrier has a central bore coupled to the projection in the first position and the projection is released from the central bore of the locking carrier in the second position. The insertion device includes a second housing having at least one locking arm coupled to the insertion set and the second housing surrounds at least a portion of the first housing to define a gap between the first housing and the second housing. The locking carrier is received in the gap in the second position to release the projection of the hub from the locking carrier and to pivot the at least one locking arm to enable the insertion set to be uncoupled from the second housing.

In various embodiments, an insertion device for use with an insertion set is provided. The insertion device includes a first housing having a rail that extends within the first housing along a longitudinal axis of the insertion device. The insertion device includes a hub having a first end coupled to the rail and a second end to be coupled to an insertion instrument. The hub is movable relative to the first housing along the rail and the second end includes a projection. The insertion device includes a locking carrier received in the first housing and movable relative to the first housing between a first position and a second position. The locking carrier has a central bore coupled to the projection in the first position and the projection is released from the central bore of the locking carrier in the second position. The central bore has a first bore diameter in the first position and a second bore diameter in the second position that is different than the first bore diameter. The insertion device includes a second housing coupled to the insertion set. The second housing surrounds at least a portion of the first housing to define a gap between the first housing and the second housing. The locking carrier is received in the gap in the second position to release the projection of the hub from the locking carrier and to enable the insertion set to be uncoupled from the second housing.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3 is a cross-sectional view of the exemplary insertion device and insertion set of FIG. 1, taken along line 3-3 of FIG. 1, in a first position;

FIG. 5 is a schematic cross-sectional view of the exemplary insertion device and insertion set of FIG. 1, taken along line 3-3 of FIG. 1, in a second position;

FIG. 6 is a schematic cross-sectional view of the exemplary insertion device and insertion set of FIG. 1, taken along line 3-3 of FIG. 1, in a third position; and FIG. 7 is a perspective view of the exemplary insertion device uncoupled from the insertion set of FIG. 1.

DETAILED DESCRIPTION

Figure 1:
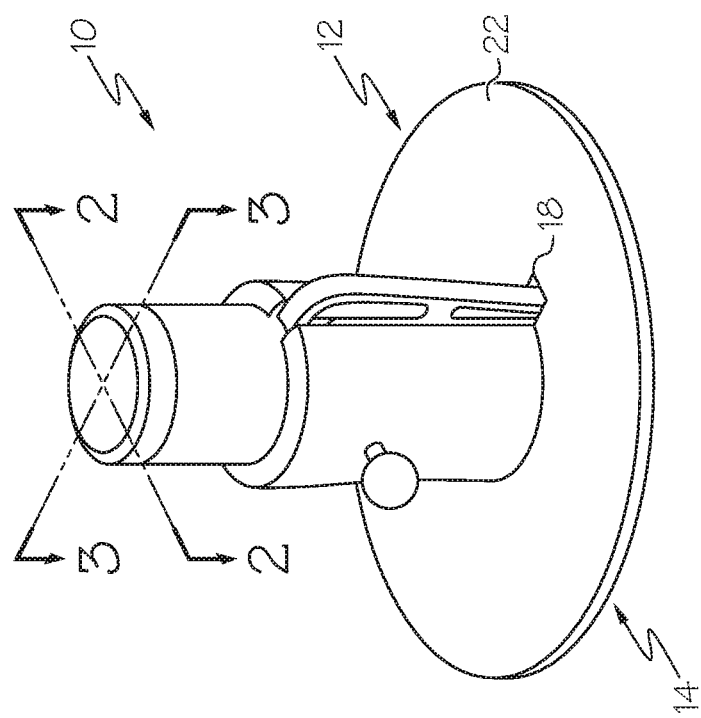
FIG. 1 is a perspective view of an exemplary embodiment of an insertion device for an insertion set according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description generally relates to an insertion set of the type used in treating a medical condition of a user. The insertion set can comprise an infusion set, for infusing a fluid into a body of the user, or can comprise a sensor set, for observing conditions associated with a fluid of the body of the user and generating sensor signals based thereon. The non-limiting examples described below relate to an insertion set used in the treatment of diabetes, although embodiments of the disclosed subject matter are not so limited. In alternative embodiments, however, many other characteristics may be treated by using the insertion set such as, but not limited to, various diseases, pulmonary hypertension, pain, anti-cancer treatments, medications, vitamins, hormones, or the like. For the sake of brevity, conventional features and characteristics related to insertion sets may not be described in detail here. Examples of insertion sets, such as sensor sets, used to observe and generate sensor signals based on blood glucose levels may be of the type described in, but not limited to: U.S. Patent Publication No. 2013/0060105; U.S. Pat. Nos. 5,299,571, 5,390,671, 5,482,473, 5,586,553 and 6,809,653, which are incorporated by reference herein. In addition, it should be note that although the following description is directed towards an insertion device for an insertion set, the insertion device described herein can be employed with any suitable device.

FIG. 1 is a perspective view of an exemplary embodiment of an insertion device 10 for coupling an exemplary insertion set 12 to a body of a user. The insertion set 12 can comprise an infusion set and/or a sensor set, which can be coupled to the body of the user by the insertion device 10 to aid in the treatment of a disease. In one example, the insertion device 10 and the insertion set 12 may be packaged together and pre-assembled to aid in coupling the insertion set 12 to the user, however, the insertion device 10 and the insertion set 12 could be packaged separately and later assembled by the user. Generally, the insertion device 10 is operated by the user to couple the insertion set 12 to the body of the user.

Figure 2:
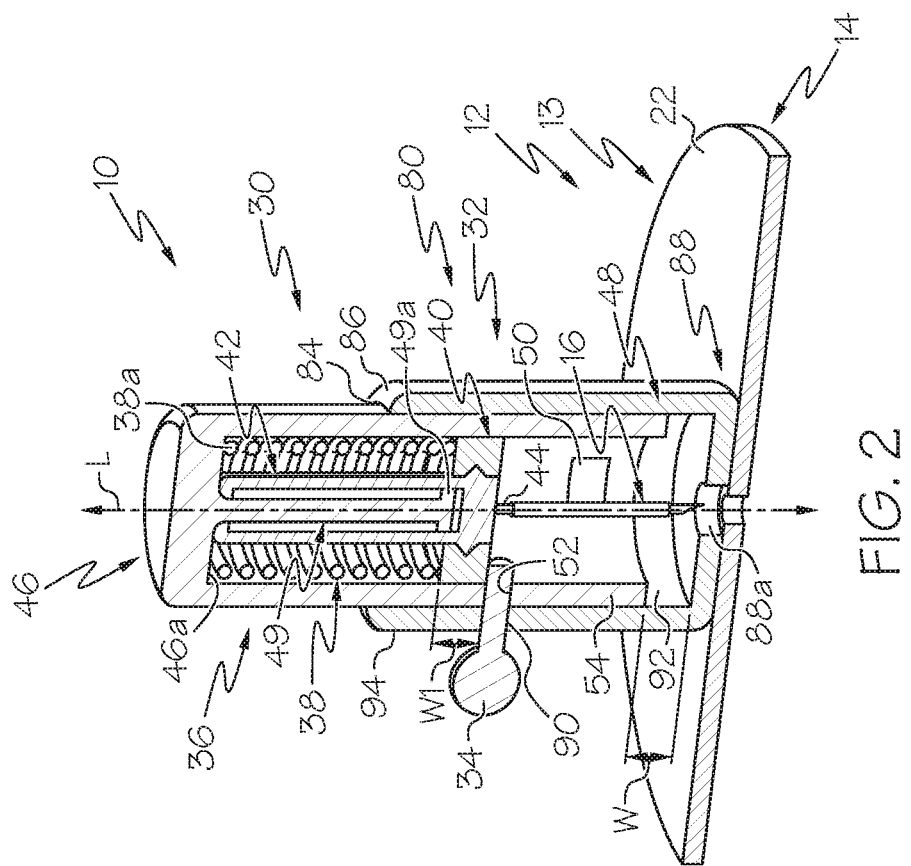
FIG. 2 is a cross-sectional view of the exemplary insertion device and insertion set of FIG. 1, taken along line 2-2 of FIG. 1.

In one of various embodiments, with reference to FIGS. 1 and 2, the insertion set 12 comprises a sensor set 13, which includes a base 14 and a sensor 16. It should be noted that the sensor set 13 illustrated herein is merely exemplary, and the sensor set 13 can include any number of additional features, including, but not limited to, a wireless transmitter, power source, cannulated tubing, etc. In one example, the sensor set 13 is any device suitable for observing glucose levels in interstitial fluid and generating sensor signals based thereon. In this example, the base 14 is illustrated herein as substantially circular, however, the base 14 may have any desired shape.

Figure 4:
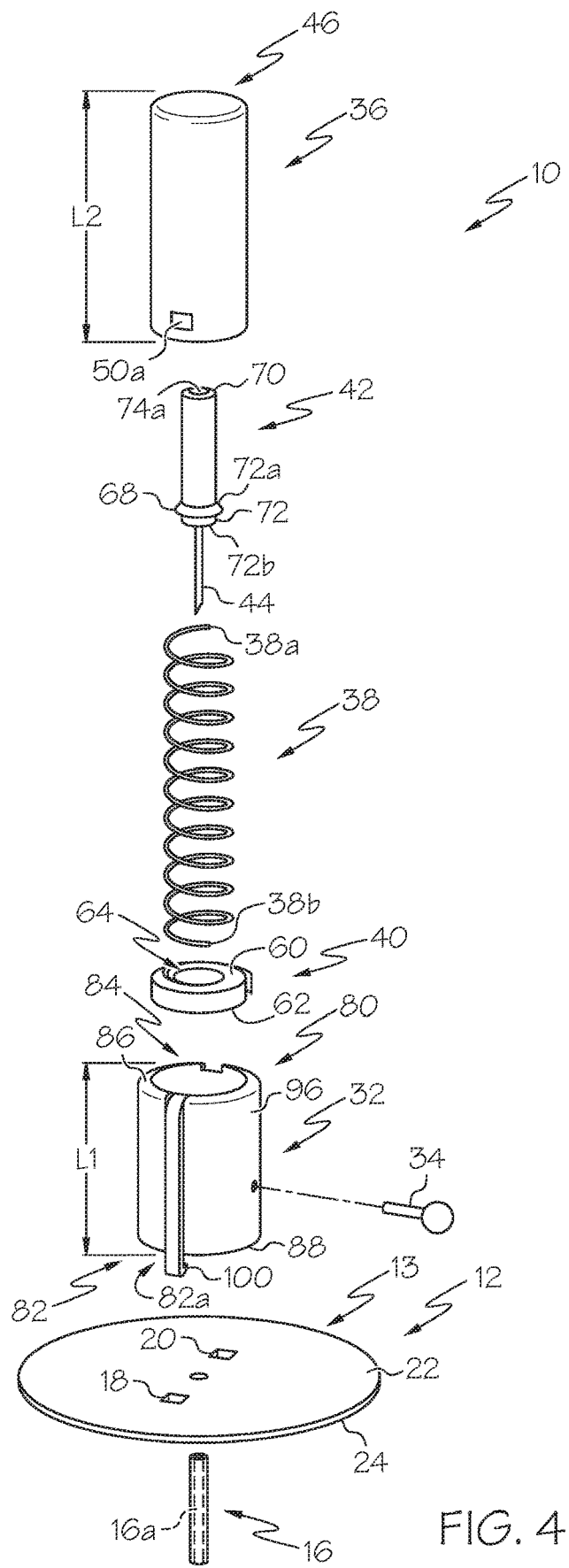
FIG. 4 is a partially exploded view of the exemplary insertion device and insertion set of FIG. 1.

With reference to FIGS. 3 and 4, the base 14 includes a first coupling aperture 18 and a second coupling aperture 20. In this example, the first coupling aperture 18 and the second coupling aperture 20 are formed substantially opposite each other about an axis of the base 14, however, as will be discussed herein, the first coupling aperture 18 and second coupling aperture 20 can be formed in any desired location on the base 14 to aid in coupling the insertion device 10 to the insertion set 12. In one example, each of the first coupling aperture 18 and second coupling aperture 20 are defined by a substantially rectangular perimeter or are substantially rectangular in shape (FIG. 4), however, the first coupling aperture 18 and second coupling aperture 20 may have any desired perimeter or shape, such as cylindrical, polygonal, etc. Furthermore, the first coupling aperture 18 and second coupling aperture 20 need not have the same perimeter or shape.

Generally, with reference to FIG. 3, the first coupling aperture 18 and second coupling aperture 20 are defined through the base 14 from a first side 22 to a second side 24 of the base 14 to facilitate the engagement of the insertion device 10 with the base 14. It should be noted, however, that the first coupling aperture 18 and second coupling aperture 20 may only be partially defined through the base 14, if desired. In addition, the second side 24 of the base 14 may also include a biocompatible adhesive to aid in coupling the base 14 to the body of the user. Further, the second side 24 of the base 14 can be coupled to a patch that includes a biocompatible adhesive to secure the base 14 to the user. The second side 24 of the base 14 can be coupled to the patch using any suitable technique, including, but not limited to, an adhesive.

In one example, the first coupling aperture 18 and second coupling aperture 20 are formed such that the sensor 16 is positioned between the first coupling aperture 18 and second coupling aperture 20. Generally, the first coupling aperture 18 and second coupling aperture 20 are substantially the same distance from the sensor 16, however, the first coupling aperture 18 or second coupling aperture 20 may be spaced a different distance from the sensor 16, if desired.

In one of various embodiments, the sensor 16 is insertable into the body of the user to observe glucose levels in interstitial fluid of the user and generate sensor signals based thereon. In one example, as will be discussed herein, the insertion device 10 is employed to insert the sensor 16 into the body of the user at a predefined depth. Once the sensor 16 is inserted into the body of the user, the insertion device 10 may be removed and disposed of, leaving the insertion set 12 coupled to the body of the user. In one example, the sensor 16 may be formed as a cannula, and may define a throughbore 16a (FIG. 5). Sensor elements may be positioned about an internal circumference of the throughbore 16a. In addition, the throughbore 16a may receive a portion of the insertion device 10 to aid in the insertion of the sensor 16 into the body of the user, as will be discussed herein.

With reference to FIG. 2, in one of various embodiments, the insertion device 10 includes a first housing or hub housing assembly 30, a second housing or shroud 32 and a trigger 34. As will be discussed, once the trigger 34 is released, the hub housing assembly 30 moves from a first position relative to the shroud 32 along a longitudinal axis L defined by the insertion device 10 to a second position to drive the sensor 16 into the body of the user. The hub housing assembly 30 is further movable from the second position to a third position for uncoupling the insertion device 10 from the insertion set 12. In one example, the hub housing assembly 30 includes a housing 36, a biasing member 38, a first member or locking carrier 40, a second member or traveling hub 42 and an insertion instrument or needle 44. It should be noted that the hub housing assembly 30 described and illustrated herein is merely exemplary, as one or more of the components may be integrated to a single component in order to insert the sensor 16 into the body of the user.

In one example, the housing 36 is substantially cylindrical and substantially symmetrical about the longitudinal axis L. It should be noted that the shape and configuration of the housing 36 described and illustrated herein is merely exemplary, as the housing 36 can have any desired shape, such as rectangular. As will be discussed herein, the housing 36 moves relative to the shroud 32. The housing 36 includes a first end 46 and a second end 48. In one example, the first end 46 is circumferentially closed to enclose the biasing member 38, locking carrier 40, traveling hub 42 and needle 44. Generally, an inner surface 46a of the first end 46 is coupled to or adjacent an end of the biasing member 38 to act as a seat for a first end 38a of the biasing member 38.

The first end 46 also includes a rail 49, which couples the traveling hub 42 to the housing 36. In one example, the rail 49 is substantially cylindrical, and extends outwardly from the inner surface 46a of the first end 46, substantially parallel to the longitudinal axis L. The rail 49 includes a T-shaped end 49a, which cooperates with the traveling hub 42 to movably couple the traveling hub 42 to the housing 36. In this example, the traveling hub 42 may be formed about the rail 49 such that the traveling hub 42 is movable or slidable on the rail 49 to the end 49a of the rail 49. It should be noted that the shape of the rail 49 is merely exemplary, as the rail 49 may have any desired shape to constrain or limit the movement of the traveling hub 42. In addition, the placement of the rail 49 within the housing 36 is merely exemplary, as the rail 49 need not be concentric with the biasing member 38 to limit the movement of the traveling hub 42.

In one embodiment, with reference to FIG. 2, the second end 48 of the housing 36 is circumferentially open to enable the needle 44 to insert the sensor 16, as will be discussed in further detail herein. Generally, the second end 48 also includes at least one notch 50 and a trigger aperture 52. With reference to FIG. 3, the at least one notch 50 enables a portion of the shroud 32 to be coupled to the housing 36 to uncouple or release the insertion device 10 from the insertion set 12, as will be discussed herein. In this example, the second end 48 includes two notches 50a, 50b, however, the second end 48 could include any number of notches 50.

The trigger aperture 52 receives the trigger 34 to fix or lock the hub housing assembly 30 in a first position. In one example, the trigger aperture 52 is defined through a sidewall 54 of the housing 36 adjacent to the second end 48 so as to be circumferentially offset from the notches 50a, 50b (FIG. 3). It should be noted that the trigger aperture 52 is merely exemplary, as any suitable mechanism may be employed to secure the hub housing assembly 30 in the first position.

With continued reference to FIGS. 2 and 3, the biasing member 38 is coupled to the housing 36 between the inner surface 46a of the first end 46 and the locking carrier 40 so as to be compressible or expandable between the first end 46 and the locking carrier 40. In one example, the biasing member 38 is a spring, including, but not limited to, a coil spring, but it should be understood that any suitable biasing member may be employed. As will be discussed further herein, generally the biasing member 38 is compressed when the hub housing assembly 30 is in the first position.

With continued reference to FIGS. 2 and 3, and with additional reference to FIGS. 4 and 5, the locking carrier 40 is movable relative to an inner surface 54a of the sidewall 54 of the housing 36 (FIGS. 2 and 3). In one example, the locking carrier 40 is composed of a resilient material, including, but not limited to, a resilient polymeric material. The locking carrier 40 is generally movable between a first, compressed position when the locking carrier 40 is within the housing 36 (FIG. 3), and a second, expanded position when the locking carrier 40 exits the housing 36 (FIG. 5).

In other words, the locking carrier 40 has a first diameter D1 in the first, compressed position (FIG. 3) and a second diameter D2 in the second, expanded position (FIG. 5), with the first diameter D1 being different than the second diameter D2. Generally, the second diameter D2 is larger than the first diameter D1. In one example, with reference to FIG. 4, the locking carrier 40 has a spiral shape, which is tightly wound in the first, compressed position and relaxed in the second, expanded position, however, the locking carrier 40 can have any desired shape, such as an accordion-like shape, for example. Furthermore, the locking carrier 40 may be press-fit into the housing 36 such that the locking carrier 40 expands when the locking carrier 40 exits the housing 36.

The locking carrier 40 has a first end 60, a second end 62 and a central bore 64 defined through locking carrier 40 from the first end 60 to the second end 62. With reference to FIG. 3, the first end 60 serves as a seat for a second end 38b of the biasing member 38. At least a portion of the second end 62 is coupled to or in contact with the trigger 34. The contact between the locking carrier 40 and the trigger 34 holds or maintains the hub housing assembly 30 in the first position. The central bore 64 receives the traveling hub 42 to couple the traveling hub 42 to the locking carrier 40 when the locking carrier 40 is in the first, compressed position. Generally, the central bore 64 includes at least one groove 66, which cooperates with corresponding at least one projection 68 of the traveling hub 42 to couple the traveling hub 42 to the locking carrier 40 when the locking carrier 40 is in the first, compressed position.

In this regard, when the locking carrier 40 is in the first, compressed position, the projection 68 of the traveling hub 42 is received and held within the groove 66 of the locking carrier 40. When the locking carrier 40 moves to the second, expanded position, with reference to FIG. 5, a diameter of the central bore 64 increases, thereby releasing the projection 68 of the traveling hub 42 from the groove 66 of the central bore 64. Stated another way, in the first, compressed position, the central bore 64 has a first bore diameter, and in the second, expanded position, the central bore 64 has a second bore diameter, which is different than the first bore diameter. As will be discussed herein, the differences between the first bore diameter and the second bore diameter enable the needle 44 to be retained and completely enclosed by the housing 36 after completion of the insertion of the sensor 16.

With continued reference to FIG. 3, the traveling hub 42 is substantially cylindrical, and includes a first end 70 and a second end 72. The first end 70 defines a bore 74 for coupling the traveling hub 42 to the rail 49 of the housing 36. In one example, the bore 74 extends from the first end 70 to a position adjacent to the second end 72, or the bore 74 extends for such a distance to receive and enclose the rail 49. The bore 74 includes a countersink 74a at the first end 70, which can be sized to enable the traveling hub 42 to move or slide relative to a portion of the rail 49. In one example, the countersink 74a is sized such that the traveling hub 42 is movable relative to the rail 49 up to the end 49a. In other words, in this example, the countersink 74a has a smaller diameter than the end 49a of the rail 49 so that the end 49a of the rail 49 serves as a stop for further movement of the traveling hub 42. It should be noted that this configuration of the traveling hub 42 and the rail 49 is merely exemplary, as any other desired mechanisms may be employed to limit the movement of the traveling hub 42 relative to the housing 36.

The second end 72 of the traveling hub 42 is coupled to the needle 44, and includes the at least one projection 68. Generally, the second end 72 is coupled to the needle 44 such that the needle 44 is substantially parallel to the longitudinal axis L. In one example, the second end 72 is formed about an end of the needle 44 to couple the needle 44 to the traveling hub 42, however, the needle 44 may be coupled to the traveling hub 42 using any desired technique, such as ultrasonic welding, adhesives, press-fit, etc.

The projection 68 extends about at least a portion of a perimeter of the second end 72, between a proximalmost end 72a of the second end 72 and a distalmost end 72b of the second end 72. The projection 68 is sized and shaped to be received within the groove 66 of the locking carrier 40. Thus, size and shape of the projection 68 and the groove 66 are merely exemplary, as any suitable cooperating engagement features may be employed between the traveling hub 42 and the locking carrier 40 to secure the traveling hub 42 with the locking carrier 40 when the locking carrier 40 is in the first, compressed position, including, but not limited to, a dovetail arrangement.

The needle 44 comprises any suitable biocompatible needle, including, but not limited to a stainless steel surgical needle. The needle 44 is coupled to the traveling hub 42, such that movement of the traveling hub 42 along the longitudinal axis L moves the needle 44 to insert the sensor 16 into the body of the user. In one example, the needle 44 is sized such that the needle 44 may be slidably received into the throughbore 16a of the sensor 16 to aid in driving the sensor 16 into the body of the user. In this example, the needle 44 imparts rigidity to the sensor 16 during insertion, and is removable or retractable from the throughbore 16a of the sensor 16 once the sensor 16 is inserted into the body of the user.

With reference to FIGS. 2-4, the shroud 32 surrounds at least a portion of the hub housing assembly 30 and couples the insertion device 10 to the insertion set 12. The shroud 32 may be composed of any suitable material, including, but not limited to a polymeric material. In one example, the shroud 32 includes a shroud housing 80 and one or more locking arms 82 (FIG. 3).

With reference to FIG. 4, the shroud housing 80 has a length L1, which is different than a length L2 of the housing 36. Generally, the length L1 is less than the length L2 of the housing 36. The shroud housing 80 defines a central housing bore 84, which extends from a first end 86 to a second end 88, and a trigger receptacle 90. The second end 88 also defines a bore 88a to enable the needle 44 to pass through the shroud housing 80 into the body of the user. The central housing bore 84 receives at least a portion of the housing 36 so that the shroud housing 80 surrounds at least a portion of the housing 36. In one example, the central housing bore 84 can have a substantially uniform surface.

Generally, with reference to FIG. 2, the housing 36 is coupled to or received within the central housing bore 84 such that a gap 92 exists between the second end 48 of the housing 36 and the second end 88 of the shroud housing 80. The gap 92 has a width W, which may be substantially equal to or slightly larger than a width W1 of the locking carrier 40, such that the locking carrier 40 is receivable within the gap 92 in the second, expanded position (FIG. 5).

With reference back to FIG. 2, the trigger receptacle 90 may be defined through a sidewall 94 of the shroud housing 80, between the first end 86 and the second end 88. In one example, the trigger receptacle 90 defines an opening through which the trigger 34 is received. Generally, the trigger receptacle 90 is aligned substantially coaxially with the trigger aperture 52 of the housing 36 so that the trigger 34 may be positioned through the shroud housing 80 and the housing 36. It should be noted that the trigger receptacle 90 is merely exemplary, as any suitable mechanism may be employed to couple the trigger 34 to the housing 36, including, but not limited to, integrally forming the trigger 34 with the shroud housing 80.

With reference to FIG. 3, the one or more locking arms 82 may extend outwardly from the shroud housing 80. In one example, the one or more locking arms 82 includes a first locking arm 82a and a second locking arm 82b, which are formed to be substantially symmetric about the longitudinal axis L. The locking arms 82 each include a lever end 96, a support 98 and a locking tab 100.

The lever end 96 biases each locking arm 82 against the first end 86 of the shroud housing 80 in a first position and couples each locking arm 82 to the notches 50a, 50b of the housing 36 in a second position. In one example, the lever end 96 includes an arcuate shape, however, the lever end 96 may have any suitable shape. As will be discussed, the lever end 96 is movable between the first position and the second position relative to the support 98 to couple and uncouple the insertion set 12 to the insertion device 10. In the first position, when the insertion set 12 is coupled to the insertion device 10, the lever end 96 is biased against the sidewall 54 of the housing 36 and in the second position, when the insertion set 12 is uncoupled from the insertion device 10, the lever end 96 is received within the notches 50a, 50b of the housing 36.

The support 98 couples each locking arm 82 to the sidewall 94 of the shroud housing 80 and serves as a pivot point for each locking arm 82. The locking tab 100 is defined at a distalmost end 102 of each locking arm 82. The locking tab 100 generally extends for a distance beyond the second end 88 of the shroud housing 80 to pass through the first coupling aperture 18 and second coupling aperture 20 of the base 14 to couple the insertion set 12 to the insertion device 10. In one example, each locking tab 100 includes a hook-like end, which hooks onto the second side 24 of the base 14 to couple the insertion set 12 to the insertion device 10.

With reference back to FIG. 2, the trigger 34 is receivable through the trigger aperture 52 of the housing 36 and the trigger receptacle 90 of the shroud housing 80. The trigger 34 maintains the hub housing assembly 30 in the first position until the user desires to insert the sensor 16. In one example, the trigger 34 is a movable locking pin, however, the trigger 34 may comprise any suitable device, which may be separate from or integral with one or more components of the insertion device 10. For example, the trigger 34 may comprise a movable portion of the shroud 32. Thus, the trigger 34 described and illustrated herein is merely exemplary.

With reference to FIGS. 2-4, in order to assemble the insertion device 10, the biasing member 38 may be inserted into the housing 36. Then, with the needle 44 coupled to the traveling hub 42 and the sensor 16 coupled to the needle 44, the traveling hub 42 is coupled about the rail 49 and the locking carrier 40 is coupled about the second end 72 of the traveling hub 42 such that the projection 68 engages the groove 66. The locking carrier 40 is positioned in the first, compressed position and with the locking arms 82 coupled to the insertion set 12, the housing 36 is inserted into the central housing bore 84, such that the hub housing assembly 30 is in the first position. Then, the trigger 34 may be inserted through the trigger receptacle 90 and trigger aperture 52 to retain the hub housing assembly 30 in the first position.

With the insertion set 12 coupled to the insertion device 10, in order to couple the insertion set 12 to the user, the second side 24 of the base 14 of the insertion set 12 may be secured to the user, using an adhesive or a patch, for example. Then, in order to insert the sensor 16, the trigger 34 may be at least partially removed. The removal of the trigger 34 from the trigger aperture 52 releases the compressed biasing member 38, which moves or biases the hub housing assembly 30 from the first position (FIG. 3) to the second position (FIG. 5). In other words, the once the trigger 34 is removed from at least the trigger aperture 52, the traveling hub 42 and the locking carrier 40 move from a position adjacent to the first end 46 of the housing 36 to a position beyond the second end 48 of the housing 36. The movement of the traveling hub 42 to the position beyond the second end 48 of the housing 36 causes the needle 44 to insert the sensor 16 into the user.

In the second position, as illustrated in FIG. 5, the countersink 74a of the traveling hub 42 of the hub housing assembly 30 is in contact with the end 49a of the rail 49, and the locking carrier 40 is received within the gap 92. As the gap 92 has a diameter larger than a diameter of the housing 36, the locking carrier 40 moves into the second, expanded position in the gap 92. Thus, the release of the trigger 34 causes the locking carrier 40 to move from the first, compressed position to the second, expanded position. The movement of the locking carrier 40 from the first, compressed position to the second, expanded position causes the groove 66 of the locking carrier 40 to disengage the projection 68 of the traveling hub 42. With the traveling hub 42 uncoupled or released from the locking carrier 40, the recoil of the biasing member 38 from contacting the locking carrier 40 with the second end 88 of the shroud housing 80, moves or drives the housing 36 upward, away from the shroud housing 80 to move the hub housing assembly 30 to the third position as illustrated in FIG. 6. The movement of the housing 36 upward, away from the shroud housing 80, moves the traveling hub 42 upward, away from the shroud housing 80 and retracts the needle 44 from the throughbore 16a of the sensor 16 into the shroud housing 80.

With continued reference to FIG. 6, during the movement of the hub housing assembly 30 to the third position, the locking arms 82 pivot and engage the notches 50a, 50b of the housing 36. The engagement of the locking arms 82 with the notches 50a, 50b moves the locking tabs 100 out of engagement with the second side 24 of the base 14 of the insertion set 12, which enables the insertion device 10 to be removed from the insertion set 12 (FIG. 7). In addition, the engagement of the locking arms 82 with the notches 50a, 50b locks the housing 36 relative to the shroud housing 80. With the housing 36 in the third position, the needle 44 is fully contained within the housing 36 and shroud housing 80, enabling proper disposal of the insertion device 10 (FIG. 6).

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An insertion device for use with an insertion set, comprising:
   a first housing having a rail that extends within the first housing along a longitudinal axis of the insertion device;
   a hub having a first end coupled to the rail and a second end to be coupled to an insertion instrument, the hub movable relative to the first housing along the rail and the second end including a projection;
   a locking carrier received in the first housing and movable relative to the first housing between a first position and a second position, the locking carrier coupled to the projection in the first position and the projection is released from the locking carrier in the second position; and
   a second housing coupled to the insertion set and surrounding at least a portion of the first housing to define a gap between the first housing and the second housing, with the locking carrier received in the gap in the second position to release the projection of the hub from the locking carrier and to enable the insertion set to be uncoupled from the second housing.

2. The insertion device of claim 1, wherein the first housing has a first housing end and a second housing end, the rail coupled to the first housing end and the rail is spaced apart from the second housing end.

3. The insertion device of claim 2, further comprising a biasing member coupled to the first housing between an inner surface of the first housing at the first housing end and the locking carrier, and the biasing member substantially surrounds the rail.

4. The insertion device of claim 3, wherein the locking carrier has a first carrier end and an opposite second carrier end, the first carrier end coupled to the biasing member and the insertion device further comprises a trigger that contacts the second carrier end to hold the locking carrier in the first position.

5. The insertion device of claim 2, wherein the rail includes a shaped end that cooperates with the first end of the hub to couple the hub to the rail.

6. The insertion device of claim 1, wherein the locking carrier has a central bore that receives the projection in the first position, the central bore having a first bore diameter in the first position, and the central bore has a second bore diameter in the second position that is different than the first bore diameter.

7. The insertion device of claim 1, wherein the second housing includes at least one locking arm that couples the insertion set to the insertion device, and the at least one locking arm pivots into engagement with the first housing to uncouple the insertion set from the second housing in the second position.

8. An insertion device for use with an insertion set, comprising:
   a first housing having a rail that extends within the first housing along a longitudinal axis of the insertion device;
   a hub having a first end coupled to the rail and a second end to be coupled to an insertion instrument, the hub movable relative to the first housing along the rail and the second end including a projection;
   a locking carrier received in the first housing and movable relative to the first housing between a first position and a second position, the locking carrier having a central bore coupled to the projection in the first position and the projection is released from the central bore of the locking carrier in the second position; and
   a second housing having at least one locking arm coupled to the insertion set and the second housing surrounding at least a portion of the first housing to define a gap between the first housing and the second housing, with the locking carrier received in the gap in the second position to release the projection of the hub from the locking carrier and to pivot the at least one locking arm to enable the insertion set to be uncoupled from the second housing.

9. The insertion device of claim 8, wherein the first housing has a first housing end and a second housing end, the rail coupled to the first housing end and the rail is spaced apart from the second housing end.

10. The insertion device of claim 9, further comprising a biasing member coupled to the first housing between an inner surface of the first housing at the first housing end and the locking carrier.

11. The insertion device of claim 10, wherein the locking carrier has a first carrier end and an opposite second carrier end, the first carrier end coupled to the biasing member and the insertion device further comprises a trigger that contacts the second carrier end to hold the locking carrier in the first position.

12. The insertion device of claim 9, wherein the rail includes a shaped end that cooperates with the first end of the hub to couple the hub to the rail.

13. The insertion device of claim 8, wherein the central bore has a first bore diameter in the first position, and the central bore has a second bore diameter in the second position that is different than the first bore diameter.

14. The insertion device of claim 8, wherein the at least one locking arm pivots into engagement with the first housing to uncouple the insertion set from the second housing in the second position.

15. An insertion device for use with an insertion set, comprising:
- a first housing having a rail that extends within the first housing along a longitudinal axis of the insertion device;
- a hub having a first end coupled to the rail and a second end to be coupled to an insertion instrument, the hub movable relative to the first housing along the rail and the second end including a projection;
- a locking carrier received in the first housing and movable relative to the first housing between a first position and a second position, the locking carrier having a central bore coupled to the projection in the first position and the projection is released from the central bore of the locking carrier in the second position, the central bore having a first bore diameter in the first position and a second bore diameter in the second position that is different than the first bore diameter; and
- a second housing coupled to the insertion set and the second housing surrounding at least a portion of the first housing to define a gap between the first housing and the second housing, with the locking carrier received in the gap in the second position to release the projection of the hub from the locking carrier and to enable the insertion set to be uncoupled from the second housing.

16. The insertion device of claim 15, wherein the first housing has a first housing end and a second housing end, the rail coupled to the first housing end and the rail is spaced apart from the second housing end.

17. The insertion device of claim 16, further comprising a biasing member coupled to the first housing between an inner surface of the first housing at the first housing end and the locking carrier, and the biasing member substantially surrounds the rail.

18. The insertion device of claim 17, wherein the locking carrier has a first carrier end and an opposite second carrier end, the first carrier end coupled to the biasing member and the insertion device further comprises a trigger that contacts the second carrier end to hold the locking carrier in the first position.

19. The insertion device of claim 16, wherein the rail includes a shaped end that cooperates with the first end of the hub to couple the hub to the rail.

20. The insertion device of claim 15, wherein the second housing includes at least one locking arm that couples the insertion set to the insertion device, and the at least one locking arm pivots into engagement with the first housing to uncouple the insertion set from the second housing in the second position.

* * * * *